United States Patent [19]

Morr et al.

[11] Patent Number: 4,845,222

[45] Date of Patent: Jul. 4, 1989

[54] PYOCYANINE DERIVATIVES AND PROCESS FOR THEIR MANUFACTURE

[75] Inventors: Michael Morr, Wolfenbüttel; Christel Kakoschke, Lahstedt; Hsin Tsai, Brunswick; Rita Getzlaff, Vechelde, all of Fed. Rep. of Germany

[73] Assignee: Gesellschaft fur Biotechnologische Forschung mbh (GBF), Brunswick, Fed. Rep. of Germany

[21] Appl. No.: 79,088

[22] Filed: Jul. 29, 1987

[30] Foreign Application Priority Data

Aug. 12, 1986 [DE] Fed. Rep. of Germany ....... 3627310

[51] Int. Cl.$^4$ .................. C07D 241/46; C07D 403/12; A61K 31/50
[52] U.S. Cl. .................................................... 544/347
[58] Field of Search ........................................ 544/347

[56] References Cited

PUBLICATIONS

Byng, Chem Abs. 86, 85997d (1976).

*Primary Examiner*—Mark L. Berch
*Attorney, Agent, or Firm*—Kane, Dalsimer, Sullivan, Kurucz, Levy, Eisele and Richard

[57] ABSTRACT

Pyocyanine compounds of the formula:

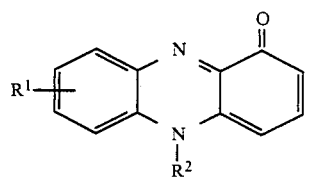

wherein $R^1$ represents one of the formula
—$C_{1-10}$-alkylene-$CO_2$-$C_{1-5}$-alkyl;
—$C_{1-10}$-alkylene-$CO_2H$; and

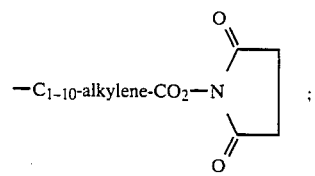

$R^2$ represents hydrogen or $C_{1-2}$-alkyl and $R^1$ is attached to the 7 or 8 aromatic ring position. The compounds are useful antibiotics.

2 Claims, No Drawings

PYOCYANINE DERIVATIVES AND PROCESS FOR THEIR MANUFACTURE

BACKGROUND OF THE INVENTION

Brief Description of the Prior Art

Pyocyanine is a blue pigment that is formed by *Pseudomonas aeruginosa*. Although it has been known for a long time that pyocyanine is bactericidally active against gram-positive and gram-negative bacteria it has not hitherto been used in the therapeutic field. The reason for this lies in the cytotoxic effect on animal cells.

The in vitro cytotoxicity of pyocyanine was able ato be confirmed in work, preceding the invention, with human fibroblasts, human lymphocytes and mouse lymphocytes in culture. The work revealed that the cytotoxicity of pyocyanine is neither cell-specific nor species-specific. To be able to use pyocyanine as a therapeutic anti-cancer agent, the inventors set themselves the task of derivatising pyocyanine in order to bond it covalently to amino group-containing water-soluble or water-insoluble polymers or oligomers, for example cellulose, dextran, dextran derivatives (such as Sephadex) or proteins, such as tumour-specific proteins, for example monoclonal antibodies.

Summary of the Invention

Pyocyanine derivatives of the following general formula are provided in accordance with the invention:

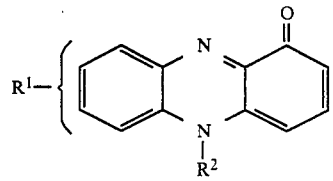

in which
$R^1 = -C_{1-10}$-alkylene-$CO_2$-$C_{1-5}$-alkyl and
$R^2 =$ H or $C_{1-2}$-alkyl, or
$R^1 = -C_{1-10}$-alkylene-$CO_2H$ and
$R^2 =$ H or $C_{1-2}$-alkyl, or

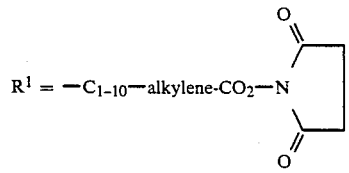

and
$R^2 =$ H or $C_{1-2}$-alkyl.

The $C_{1-10}$-alkylene group in the radical $R^1$ may be an ethylene, propylene or butylene radical.

DETAILED DESCRIPTION OF THE PREFERRED EMBODIMENTS OF THE INVENTION

The process of the invention is set forth schematically in the formulae:

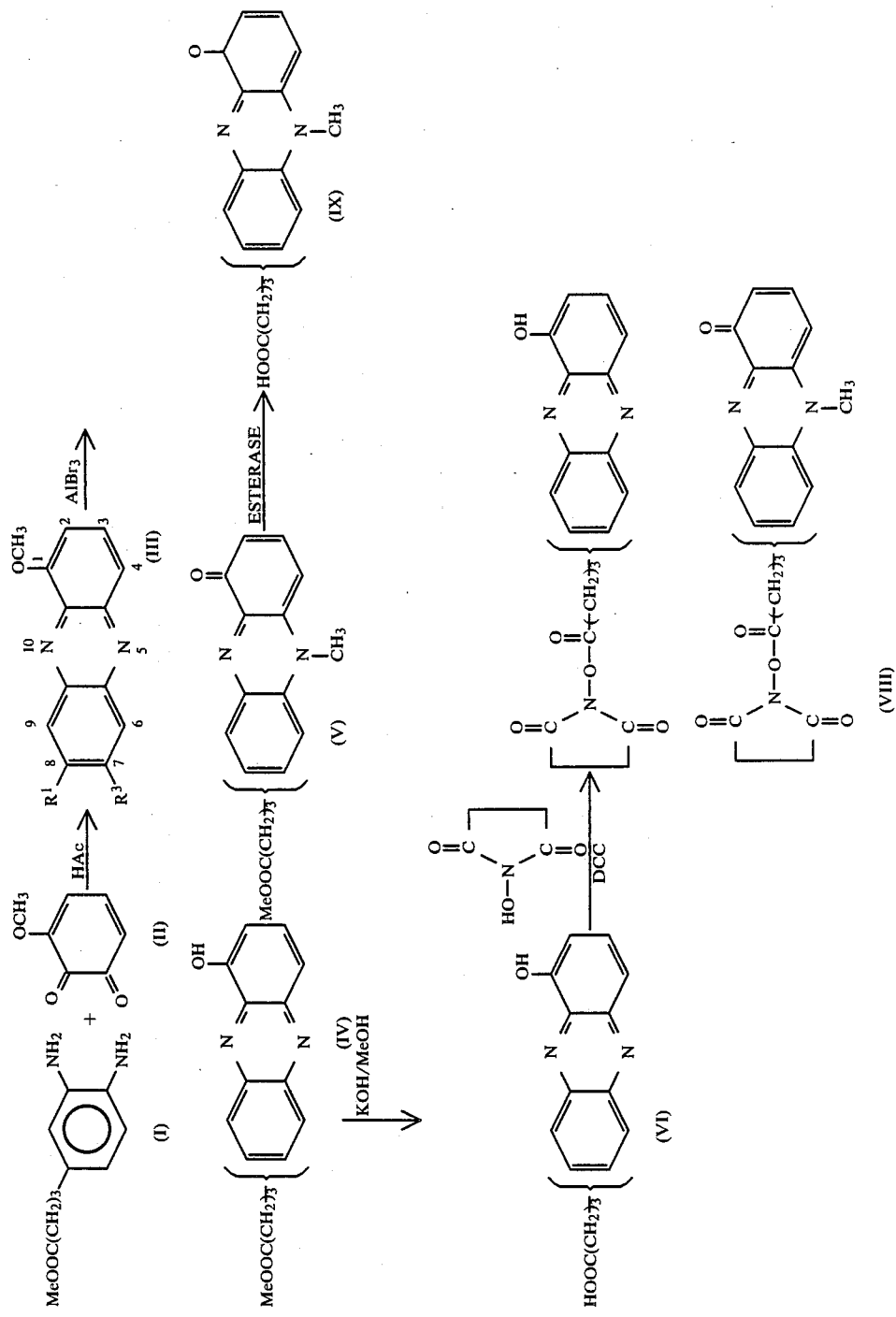

wherein $R^1$ represents —CH$_2$(CH$_2$)$_2$COOMe and $R^3$ is hydrogen or $R^1$ represents hydrogen and $R^3$ is a group of the formula —CH$_2$(CH$_2$)$_2$COOMe.

ω-(3,4-Diaminophenyl)-C$_{1-10}$-alkanoic acid C$_{1-5}$-alkyl esters of formula (I) are used as starting materials for the manufacture of the pyocyanine derivatives according to the invention. 4'-(3,4-Diaminophenyl)-butyric acid methyl ester is known; see Aharoni & Litt, J. Polym. Sci., Polymer Chemistry Edition, 12 (1974) 639. The other ω-(3,4-diaminophenyl)-C$_{1-10}$-alkanoic acid C$_{1-5}$-alkyl esters (I) used as starting materials according to the invention may be manufactured analogously to the prior art indicated.

The invention also relates to a process for the manufacture of the pyocyanine derivatives according to the invention in which (a) ω-(3,4-diaminophenyl)-C$_{1-10}$-alkanoic acid C$_{1-5}$-alkyl ester (I) is reacted with 3-C$_{1-2}$-alkoxy-o-quinone (II) to form ω-(1-C$_{1-2}$-alkoxy-phenazin-$\frac{7}{8}$-yl)-C$_{1-10}$-alkanoic acid C$_{1-5}$-alkyl esters (III) and (b) the resulting product (III) is treated with aluminium bromide in an inert organic solvent to obtain corresponding compounds of the formulae (IV) or (V); and if desired, (c) the resulting product is hydrolysed to the free acid (VI) or (IX) and, if desired, (d) the resulting free acid (VI) is alkylated to the pyocyanine derivative (IX), or is reacted with N-hydroxysuccinimide or N-hydroxyglutaric acid imide and pyocyanine derivatives of the general formula (VII) given above in which

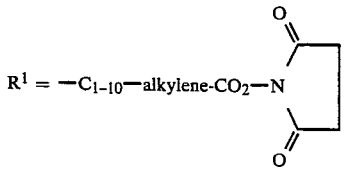

and
$R^2$=H are obtained, and, if desired, (e) the resulting product (VII) is alkylated to pyocyanine derivatives of the general formula (VIII) in which

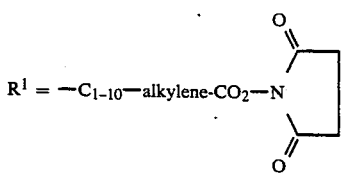

and
$R^2$=C$_{1-2}$-alkyl.

The hydrolysis of step (c) can be in the case of the product (V) be carried out carefully with esterase.

The pyocyanine derivatives according to the invention are 1:1 mixtures of positional isomers that are substituted in the 7- or 8-position of the phenazine ring. The positional isomers may be separated by gas chromatography. If they are to be used further, separation does not, however, seem necessary, since the two positional isomers have in common the structural element responsible for the antibiotic action against gram-positive and gram-negative bacteria.

In the following, the invention is explained in detail by Examples.

EXAMPLE 1

4'-(1-Methoxy-phenazin-$\frac{7}{8}$-yl)-butyric acid methyl ester (III)

2.2 g (10.6 mmol) of 4'-(3,4-diaminophenyl)-butyric acid methyl ester (I) are dissolved in 14.1 ml of glacial acetic acid and 35 ml of anhydrous benzene and quickly added dropwise to a solution of 2 g (14.5 mmol) of 3-methoxy-o-quinone (II) in 700 ml of benzene. After approximately 5 hours the reaction mixture is extracted by shaking three times with 200 ml of water each time, twice with 100 ml of saturated sodium bicarbonate solution each time and twice with 200 ml of water each time. The yellow benzene solution is dried with sodium sulphate and concentrated to dryness.

Yield: 2.8 g (85% of the theoretical yield) of crude product.

Further purification was carried out on a silica gel column (39×5 cm) with elution in stages with dichloromethane and dichloromethane/methanol mixtures 98.5:1.5/95:5/92.5:7.5.

Yield: 2.04 g (62% of the theoretical yield).

The positional isomers of (III) and can be separated by gas chromatography on a capillary column having a methyl silicone phase. GC-MS (gas chromatography mass spectrum) indicated a mass of 310 (C$_{18}$H$_{18}$N$_2$O$_3$ molecular weight=310.35).

EXAMPLE 2

4'-(1-Hydroxy-phenazin-$\frac{7}{8}$-yl)-butyric acid methyl ester (IV)

1.2 g (3.87 mmol) of (III) are dissolved in approximately 250 ml of dry benzene and, while stirring and with the exclusion of moisture, a solution of approximately 6 g of anhydrous aluminium bromide in 200 ml of benzene is added. After approximately 3 hours the brown solution is concentrated to dryness and ice and ethyl acetate are carefully added. The aqueous violet solution (pH 3.3) is extracted five times with 50 ml of ethyl acetate each time. The green-yellow ethyl acetate extract is dried with sodium sulphate and concentrated to dryness. 1.01 g the compound of formula (IV) (88% of the theoretical yield) is obtained.

The aqueous violet solution is adjusted to pH 9 and extracted with chloroform. The blue chloroform extract is covered over with a layer of aqueous hydrochloric acid and shaken. The aqueous violet solution is separated off, again adjusted to pH 9, and the blue by-product of formula (V) is extracted with chloroform.

Yield: 0.14 g of (V).

EXAMPLE 3

4'-(1-Hydroxy-phenazin-$\frac{7}{8}$-yl)-butyric acid (VI).

3 g (10 mmol) of compound of the formula (IV) are dissolved in 50 ml of 25% methanolic potassium hydroxide solution and the whole is left to stand at room temperature for 3 hours. The red-violet solution is adjusted to pH 4 with 10% hydrochloric acid in an ice bath (yellow colour). After removal of the methanol in a rotary evaporator, the aqueous solution is extracted by shaking five times with 60 ml of ethyl acetate each time. Drying with sodium sulphate and concentration to dryness yields approximately 2.55 g (89% of the theoretical yield) of compound of the formula (VI).

$C_{16}H_{14}N_2O_3$ (282.3)

|  | C | H | N |
|---|---|---|---|
| Calc. | 68.07 | 5.00 | 9.92 |
| Found | 67.87 | 5.11 | 10.13 |

EXAMPLE 4

4'-(1-Hydroxy-phenazin-⅞-yl)-butyric acid N-hydroxy-succinimide ester (VII)

214 mg (1.86 mmol) of N-hydroxysuccinimide and 384 mg (1.86 mmol) of dicyclohexylcarbodiimide (DCC) are added to 0.5 g (1.8 mmol) of compound (VI) dissolved in 130 ml of anhydrous ethyl acetate. The whole is stirred overnight, the precipitated dicyclohexyl urea is removed by filtration and the filtrate is concentrated to dryness. For further reactions, the not quite clean product ($\approx$0.6 g) is dissolved in anhydrous dimethyl-formamide and stored in a refrigerator.

EXAMPLE 5

4'-(1-Keto-5(N)-methylphenazin-⅞-yl)-butyric acid N-hydroxysuccinimide ester (VIII)

2 ml of freshly distilled dimethyl sulphate are added to 60 mg ($\approx$0.16 mmol) of compound of the formula (VII) and the whole is heated at 100° C. for 10 minutes. The whole is then cooled in ice and ether is added. The brown precipitate is suction-filtered off over a frit, washed with ether and dissolved in saturated sodium bicarbonate solution. The solution is extracted by shaking with chloroform, and the blue chloroform phase is washed with aqueous hydrochloric acid (pH 3). The red-violet aqueous phase is separated off, made alkaline with saturated sodium bicarbonate solution and again extracted by shaking with chloroform. Drying is carried out with sodium sulphate and, after concentration to dryness, approximately 10 mg ($\approx$16% of the theoretical yield) of compound of the formula (VIII) are obtained.

EXAMPLE 6

4'-(1-Keto-5(N)-methylphenazin-⅞-yl)-butyric acid (IX)

3 mg of compound (V) are dissolved in 0.5 ml of 0.1M phosphate buffer (pH 8) and 5 ul of esterase (Boehringer) are added. The whole is left to stand at 25° C., and the cleavage of the methyl ester is controlled using thin layer chromatography on silica gel (eluant: $CH_2Cl_2$:MeOH 9:1). After one hour the cleavage is complete. The product is adjusted to pH 5, concentrated to dryness and the free acid is extracted with a small amount of methanol.

Yield: approximately 2 mg of compound of formula (IX).

What is claimed is:

1. Pyocyanine compounds of the formula:

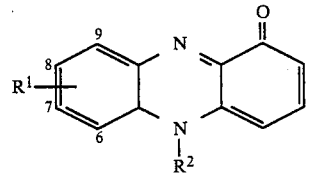

wherein
R[1] represents a monovalent moiety selected from those of the formulae
—$C_{1-10}$-alkylene-$CO_2$-$C_{1-5}$-alkyl;
—$C_{1-10}$-alkylene-$CO_2H$; and

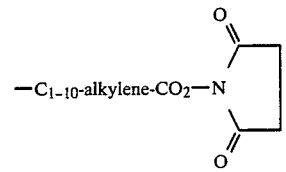

and
R[2] represents H or $C_{1-2}$-alkyl;
and wherein R[1] is attached to a ring carbon at the 7 or 8 position.

2. Pyocyanine derivatives according to claim 1, characterised in that $C_{1-10}$-alkylene is an ethylene, propylene or butylene radical.

* * * * *

UNITED STATES PATENT AND TRADEMARK OFFICE
CERTIFICATE OF CORRECTION

PATENT NO. : 4,845,222
DATED : July 4, 1989
INVENTOR(S) : Michael Morr et al

It is certified that error appears in the above-identified patent and that said Letters Patent is hereby corrected as shown below:

Columns 3 and 4; between the formulae VI and VIII insert

-- (VII)  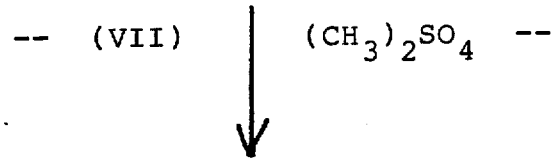 --

Signed and Sealed this

Twenty-seventh Day of November, 1990

Attest:

HARRY F. MANBECK, JR.

*Attesting Officer*     *Commissioner of Patents and Trademarks*